US012653807B2

(12) United States Patent
Galli et al.

(10) Patent No.: US 12,653,807 B2
(45) Date of Patent: Jun. 16, 2026

(54) MODIFIED RELEASE FORMULATION FOR (-)-(3AR,4S,7AR)-4-HYDROXY-4-M-TOLYLETHYNYL-OCTAHYDRO-INDOLE-1-CARBOXYLIC ACID METHYL ESTER

(71) Applicant: NOVARTIS AG, Basel (CH)

(72) Inventors: Bruno Galli, Seltisberg (CH); Jean-Marie Glantzmann, Michelbach-le-Bas (FR); Arnaud Grandeury, Helfrantzkirch (FR); Klaus-Peter Moll, Basel (CH); Martin Mueller-Zsigmondy, Freiburg (DE); Karsten Putzbach, Basel (CH); Dirk Spickermann, Staufen (DE); Hubert Thoma, Pfaffenweiler (DE); Mike Ufer, Allschwil (CH)

(73) Assignee: NOVARTIS AG, Basel (CH)

( * ) Notice: Subject to any disclaimer, the term of this patent is extended or adjusted under 35 U.S.C. 154(b) by 573 days.

(21) Appl. No.: 16/898,071

(22) Filed: Jun. 10, 2020

(65) Prior Publication Data

US 2021/0069150 A1 Mar. 11, 2021

Related U.S. Application Data

(63) Continuation of application No. 14/897,439, filed as application No. PCT/IB2014/062136 on Jun. 11, 2014, now abandoned.

(60) Provisional application No. 61/834,104, filed on Jun. 12, 2013.

(51) Int. Cl.

| | |
|---|---|
| ***A61K 31/404*** | (2006.01) |
| ***A61J 3/02*** | (2006.01) |
| ***A61J 3/10*** | (2006.01) |
| ***A61K 9/16*** | (2006.01) |
| ***A61K 9/20*** | (2006.01) |
| ***A61K 9/28*** | (2006.01) |
| ***A61K 9/50*** | (2006.01) |
| ***A61K 31/4045*** | (2006.01) |
| ***A61K 47/38*** | (2006.01) |

(52) U.S. Cl.

CPC ............... *A61K 31/404* (2013.01); *A61J 3/02* (2013.01); *A61J 3/10* (2013.01); *A61K 9/1652* (2013.01); *A61K 9/1682* (2013.01); *A61K 9/2004* (2013.01); *A61K 9/2072* (2013.01); *A61K 9/28* (2013.01); *A61K 9/50* (2013.01); *A61K 9/5089* (2013.01); *A61K 31/4045* (2013.01); *A61K 47/38* (2013.01)

(58) Field of Classification Search

None

See application file for complete search history.

(56) References Cited

U.S. PATENT DOCUMENTS

| | | | | |
|---|---|---|---|---|
| 7,348,353 | B2 | 3/2008 | Gasparini ............ | C07D 209/08 514/419 |
| 2006/0216347 | A1 | 9/2006 | Stroppolo ............ | A61K 9/2095 424/464 |
| 2008/0207749 | A1 | 8/2008 | Rouzade-Dominguez et al. | |
| 2009/0215744 | A1 | 8/2009 | Brown ................... | A61K 9/009 514/211.13 |
| 2012/0039999 | A1 | 2/2012 | Chatterji et al. | |
| 2012/0040008 | A1 | 2/2012 | Chatterji et al. | |

FOREIGN PATENT DOCUMENTS

| | | | |
|---|---|---|---|
| CN | 101222921 | A | 7/2008 |
| CN | 103068372 | A | 4/2013 |
| JP | 2005-514381 | A | 5/2005 |
| WO | 2003/047581 | A1 | 6/2003 |
| WO | 2010048095 | A2 | 4/2010 |
| WO | 2012139876 | A1 | 10/2012 |

OTHER PUBLICATIONS

Amidon et al. A theoretical basis for a biopharmaceutic drug classification: The correlation of in vitro drug product dissolution and in vivo bioavailability. Pharm Res 1995;12:413-20.

Kocbek et al., Int J Pharm. Apr. 7, 2006;312(1-2):179-86.

Shuji Kitagawa, Basic Yakugaku-Kyohasho (Pharmacology Textbook), Series 20, Yakuzaigaku (Pharmaceutics), Second Edition, Kagaku-Dojin Publishing Co., Inc., 2012, pp. 169-175 (a document indicating a well-known technology).

English Translation of Japanese Office Action dated Mar. 20, 2018 in Japanese Patent Application No. 2016-518626.

Kerper et al. (PLOS One, 7(12), e5167-e51167, 2012) Persistence of Psychological Distress in . . .

Nokhodchi et al. (Biolmpacts, 2(4) 1-13, 2012) The role of Oral Controlled . . .

Notification of the First Office Action in corresponding CN 202010410902.8 dated Sep. 29, 2023 (pp. 1-6) and english translation thereof.

*Primary Examiner* — Tigabu Kassa

(74) *Attorney, Agent, or Firm* — POLSINELLI PC

(57) ABSTRACT

Drug products in the form of modified release formulations comprising the drug substance (−)-(3aR,4S,7aR)-4-Hydroxy-4m-tolylethynyl-octahydro-indole-1-carboxylic acid methyl ester (AFQ056), as well as processes for making such drug products are provided. The drug products are useful in treating patients with Parkinson's disease and exhibiting L-dopa induced dyskinesia.

5 Claims, 22 Drawing Sheets

Dissolution Profile

Form A 100 mg

In Vitro – In Vivo Correlation (IVIVC): mechanistic PK model

Calculated (symbols) versus observed (lines) plasma concentration

Form B 100 mg

In Vitro – In Vivo Correlation (IVIVC): mechanistic PK model

Calculated (symbols) versus observed (lines) plasma concentration

Capsules 50 mg

In Vitro – In Vivo Correlation (IVIVC): mechanistic PK model

Calculated (symbols) versus observed (lines) plasma concentration

PK parameters:

| | $AUC_{48h}$ [h*ng/mL] (observed) | $C_{max}$ [ng/mL] (observed) |
|---|---|---|
| Form A 100 mg | 1440 (1438) | 145.2 (159.3) |
| Form B 100 mg | 1046 (1317) | 109.3 (99.5) |
| Capsule 50 mg | 865 (745) | 115.9 (119.7) |

Fig. 1E

Dissolution profile: Immediate release Form (IR) Capsule 50 mg

Simulated (line) plasma concentration profile is compared to the observed plasma concentration profile of the 50 mg capsule (symbols)

| | Tmax [h] | Cmax [ng/mL] | $AUC_{48h}$ [h*ng/mL] |
|---|---|---|---|
| Capsule 50 mg in study X2167 | 1.0 | 115.9 | 865 |
| Simulation hPK from Capsule 50 mg in dissolution medium + 40% EtOH | 0.4 (faster) | 130.1 (higher) | 947 (higher) |

Simulated PK parameters compared to human data

Fig. 5C

Dissolution profile: Immediate release Form (IR) Capsule 400 mg

Simulated (line) plasma concentration profile is compared to the observed plasma concentration profile of the 400 mg capsule (symbols)

| | Tmax [h] | Cmax [ng/mL] | $AUC_{48h}$ [h*ng/mL] |
|---|---|---|---|
| Capsule 400 mg in study X2101 | 3.48 | 315 | 1980 |
| Simulation h-PK from Capsule 400 mg in dissolution medium + 40% EtOH | 0.4<br>(faster) | 997.1<br>(higher) | 7249<br>(higher) |

Simulated PK parameters

Fig. 6C

Dissolution Profile: Modified Release (MR) tablet cores of 200 mg

Simulated (line) plasma concentration profile compared to human PK data of MR Form B (symbols) observed

| | Tmax [h] | Cmax [ng/mL] | $AUC_{48h}$ [h*ng/mL] |
|---|---|---|---|
| MR tablet Form B 100mg in study X2167 | 4.0 | 99.5 | 1046 |
| Simulation h-PK fromMR tablet 200 mg in dissolution medium + 40% EtOH (normalized to 100 mg) | 3.5 (almost equal) | 95.6 (almost equal) | 905 (lower) |

Simulated PK parameters compared to human data

Fig. 7C

| Time | Declared content in % | | | | | | | | |
|---|---|---|---|---|---|---|---|---|---|
| X145 [min] | start | X377 time [min] | start | X328 time [min] | start | X329 time [min] | start | X077 time [min] | start |
| 0 | 0 | 0 | 0 | 0 | 0 | 0 | 0 | 0 | 0 |
| 15 | 65.6 | 60 | 14.7 | 60 | 17.9 | 120 | 22.7 | 15 | 4.5 |
| 30 | 84.5 | 120 | 30.2 | 180 | 54.7 | 240 | 49.6 | 30 | 13.1 |
| 45 | 90.8 | 240 | 65.7 | 300 | 83.7 | 300 | 62.6 | 45 | 24.9 |
| 60 | 93.5 | 420 | 96.8 | 360 | 95.5 | 420 | 84.0 | 60 | 41.9 |
| 75 | 96.0 | 480 | 96.5 | 420 | 98.2 | 480 | 93.5 | | |

Method: - paddle, 0.5% LDAO in water, 900 ml, 100 rpm (X377, X328, X329)
- paddle, 0.5% LDAO in water, 900 ml, 75 rpm (X145)
- paddle, 0.5% SDS in water, 1000 ml, 50 rpm (X077)

Fig. 8B

PK Results

Particle size distribution

| | x10 | x50 | x90 |
|---|---|---|---|
| 0919019 | 2 | 7 | 26 |
| 0829009 | 8 | 33 | 77 |
| 1014036 | 8 | 40 | 101 |
| C0003 V1 | 5 | 37 | 128 |
| 1014031 | 9 | 50 | 132 |
| 1014041 | 10 | 50 | 135 |
| C0002 V5 | 6 | 40 | 151 |
| C0009 | 12 | 66 | 164 |
| C0002 V3 | 7 | 44 | 165 |
| 1013043 | 6 | 43 | 180 |
| C0002 V1 | 8 | 53 | 191 |
| C0001 V1 | 12 | 77 | 243 |
| 1019034 | 26 | 123 | 317 |
| 101403 | 285 | 515 | 747 |

MODIFIED RELEASE FORMULATION FOR (-)-(3AR,4S,7AR)-4-HYDROXY-4-M-TOLYLETHYNYL-OCTAHYDRO-INDOLE-1-CARBOXYLIC ACID METHYL ESTER

BACKGROUND OF THE INVENTION

The drug substance AFQ056 is a subtype-selective, non-competitive antagonist at the metabotropic glutamate receptor 5 (mGluR5). Glutamate is the main excitatory neurotransmitter in the nervous system and as such is involved in a variety of physiological and pathophysiological functions. Excessive glutamatergic transmission has been shown to play a role in both movement disorders and psychiatric conditions and the pharmacological use of glutamate receptor antagonists has shown efficacy in these indications.

The systemic chemical name for AFQ056 is (−)-(3aR,4S,7aR)-Octahydro-4-hydroxy-4-[(3-methylphenyl)ethynyl]-1H-indole-1-carboxylic acid methyl ester, and is also known as (−)-(3aR,4S,7aR)-4-Hydroxy-4m-tolylethynyl-octahydro-indole-1-carboxylic acid methyl ester. AFQ056 has the molecular formula $C_{19}H_{23}NO_3$ and the following structural formula:

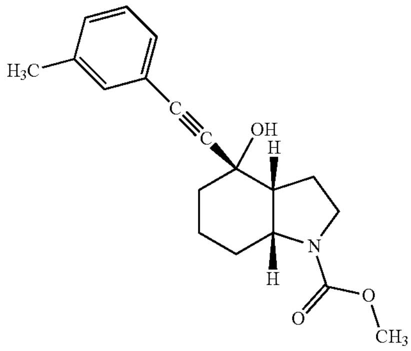

AFQ056 drug substance is a white to practically white powder, which is hardly soluble in water but soluble in organic solvents (distribution coefficient is Log P=4.7). AFQ056 is a chiral molecule with 3 asymmetric carbon atoms and has a melting point of about 115° C. One single polymorph has been identified.

WO 03/047581 describes the preparation of AFQ056 and its use as a pharmaceutical, especially in the treatment of nervous system disorders including Parkinson's disease. Parkinson's disease (PD) is a degenerative movement disorder that affects approximately 100-250 cases per 100,000 individuals. Treatment with L-dopa, a precursor of dopamine, constitutes the mainstay and gold standard in the treatment of PD. One of the major problems associated with long-term L-dopa treatment is the development of L-dopa induced motor complications such as dyskinesias (LIDs).

AFQ056 has previously been formulated as a hard gelatin capsule and as a powder for oral suspension, both with immediate release (IR) properties. Results in Parkinson's disease patients administered AFQ056 demonstrate a reduction in L-dopa induced dyskinesias without inducing any clinically or statistically significant worsening of the underlying Parkinsonian motor symptoms. The most frequent adverse events observed in patients are in the nervous system and psychiatric system organ class, including dizziness, dyskinesia, nausea, fatigue, and hallucinations. Results also revealed that a significant proportion of patients did not achieve and maintain the target dose throughout the study, presumably due to tolerability issues such as dizziness. The IR formulation used in these studies required twice-daily dosing.

Advantages of modified release formulations are the prolonged blood plasma levels of drug compared to an immediate release formulation. Modified release formulations usually contain more of the drug than the single dose administered in an immediate release dose form. If the formulation releases the drug at a rate that is faster than the intended controlled release rate (often referred to as dose dumping), there is a risk of overdosing with potential severe consequences for the patient.

An additional safety concern can occur where the drug may interact with alcohol (ethanol) and lead to changes in the pharmacokinetic pattern. Oral formulations are often taken with a commonly available beverage such as water, carbonated beverage etc. or occasionally with an alcohol-containing (ethanol-containing) beverage. Dose dumping needs to be prevented also when the patient consumes alcoholic beverages hours after ingestion of the modified release formulation. Dose dumping needs to be prevented also when patients desire to abuse a drug due to its inherent side effects, like hallucinations etc.

US 2003/0118641 relates to abuse-resistant sustained release opioid formulations using an ionic exchange resin. WO 2008/086804 describes the preparation of pharmaceutical compositions comprising polyglycols that mitigate the risk of alcohol induced dose dumping and that reduce the risk of drug abuse. US 2008/0085305 refers to robust sustained release formulations based on hydrophilic gums that resist dose dumping when ingested with alcohol. Roberts et al. (Int. Journal of Pharmaceutics 2007, 332, p. 31-37) describe the influence of ethanol on an oral dosage form comprising hypromellose matrices and aspirin. To the best of the inventors' knowledge no modified release formulation has been developed that takes into account the specificities of AFQ056 and at at the same time eliminates the risk for alcohol induced does dumping after co-ingestion.

Therefore, there is a need for a safe modified release formulation, preferably a once daily dose, with a lowered Cmax/AUC ratio relevant for tolerability, efficacy and compliance, thus allowing more patients to be treated with clinically efficacious doses of AFQ056. Furthermore, there is a need for a pharmaceutical formulation that prevents drug abuse, in particular regarding a concomitant consumption of alcoholic beverages.

SUMMARY OF THE INVENTION

The present invention provides drug products comprising AFQ056 having modified drug substance release properties. In one embodiment of the invention there is provided a modified release formulation comprising (−)-(3aR,4S,7aR)-4-Hydroxy-4m-tolylethynyl-octahydro-indole-1-carboxylic acid methyl ester in free base form, and a modified release agent, preferably hydroxy propyl methylcellulose (also known as hypromellose), together with one or more pharmaceutically acceptable excipients.

In one embodiment of the invention there is provided a modified release formulation comprising (−)-(3aR,4S,7aR)-4-Hydroxy-4m-tolylethynyl-octahydro-indole-1-carboxylic acid methyl ester in free base form as active pharmaceutical ingredient and a modified release agent, preferably hydroxyl propyl methylcellulose, such that the active pharmaceutical ingredient is released from the formulation in a controlled fashion over a period of 6 hours, or over a period of 7 hours, so that at least 80% of the active pharmaceutical ingredient has been released at the end of this period.

The drug products in the form of modified release formulations of the present invention release AFQ056 in a range of from about 14% to about 20% after 60 minutes; about 51% to about 61% after 180 minutes; about 67% to about 77% after 240 minutes; about 90% to about 95% after 360 minutes; and about 95% to about 99% after 420 minutes.

In another embodiment of the invention there is provided a modified release formulation comprising (−)-(3aR,4S,7aR)-4-Hydroxy-4m-tolylethynyl-octahydro-indole-1-carboxylic acid methyl ester in free base form that exhibits a similar or decreased release rate in ethanol containing media as compared to a purely aqueous media.

The drug substance has a particle size distribution of $\times10\leq50$ μm, $\times50\leq100$ μm and $\times90\leq200$ μm.

In one embodiment of the invention, the drug products of the present invention are single unit dosage forms with AFQ056 present in an amount of about 25 mg to about 250 mg. In a preferred embodiment, AFQ056 is present in an amount of about to about 200 mg, more preferably in an amount of about 75 to 150 mg, more preferably in an amount of about 100 mg.

In another embodiment, the pharmaceutical composition comprises a coating.

In a further embodiment a single unit dosage form is provided comprising about 25 mg to about 250 mg AFQ056, about 69 mg to about 135 mg hypromellose (type 2208 characterized by viscosities between about 80 to about 120 cP (2% in water at 20° C.)) about 20 mg to about 160 mg lactose monohydrate, about 3 mg to about 38 mg sodium starch glycolate, about 2 mg to about 4.5 mg Magnesium stearate and about 1 mg to about 2.2 mg colloidal silicon dioxide.

In another embodiment, the drug product is a pharmaceutical composition comprising (−)-(3aR,4S,7aR)-4-Hydroxy-4m-tolylethynyl-octahydro-indole-1-carboxylic acid methyl ester in the form of a single unit dosage form comprising equal to or less than 100 mg AFQ056 compressed to round tablets with a diameter of about 8 mm. In still another embodiment, the drug product comprising AFQ056 is in the form of a single unit dosage form comprising more than 100 mg AFQ056 compressed to round tablets with a diameter of about 11 mm.

In another embodiment of the invention, there is provided a process for the production of a composition comprising AFQ056 and having modified release properties. The process comprises (i) mixing AFQ056 with filler, binder and disintegrant in a high shear granulator
(ii) adding purified water under mixing
(iii) kneading the mixture in a high shear granulator
(iv) passing the granulate through a screen using a screening mill
(v) drying the granulate in a fluid bed dryer
(vi) mixing the dry granulate with a modified release agent, filler and glidant in a diffusion mixer followed by consecutive sieving and mixing
(vii) sieving a lubricant and adding to the mixture from step (vi)
(viii) final mixing the mixture from step (vii) in a diffusion mixer.
(ix) forming the composition.

In another embodiment of the invention there is provided the use of a modified release formulation in the manufacture of a medicament for the treatment of Parkinson's disease L-dopa induced dyskinesia, Fragile X syndrome (Martin-Bell syndrome), dyskinesia in Fragile X syndrome, obsessive compulsory disorders, autism, cystitis, and for the treatment, prevention or delay of progression of acute, traumatic and chronic degenerative processes of the nervous system, such as Parkinson's disease, senile dementia, Alzheimer's disease, Huntington's chorea, amyotrophic lateral sclerosis and multiple sclerosis, diseases such as schizophrenia and anxiety, depression, pain, itch and drug abuse such as alcohol and nicotine abuse and cocaine use disorders.

Also provided is a method of treating a patient with Parkinson's disease and exhibiting L-dopa induced dyskinesia, by administering an effective amount of a pharmaceutical composition of the present invention.

In another embodiment there is provided a method of treating a patient with Parkinson's disease and exhibiting L-dopa induced dyskinesia, which comprises administering to said patient an effective amount of the drug product comprising AFQ056 with a modified release profile of Cmax/AUC of about, 0.08 to about 0.18 and a Tmax of about 4 hours to about 6 hours.

BRIEF DESCRIPTION OF THE DRAWINGS

FIG. 1 shows the validity of the used prediction model. The measured in-vitro profiles together with the model (not shown) allow to predict the human profiles derived from the in-vitro modified release and immediate release-formulation dissolution data.

FIG. 2 shows that raising ethanol levels in the pure aqueous solution lead to a steadily increasing solubility of AFQ056. Up to the amount of about 20% of ethanol in the solutions, the LDAO (Lauryldimethylamine N-oxide) in water solution and the water-ethanol solution show a different solubility pattern of AFQ056. In the presence of about 40% ethanol in the solutions, both the LDAO in water solution and the water-ethanol solution show a similar solubility for AFQ056.

FIG. 5 shows also that in the simulation of human PK parameters (simulation of human PK applying the in-vitro in-vivo correlation model) the Tmax value in the ethanol containing solution is achieved faster and the Cmax and the $AUC_{48h}$ are both higher compared to the observed plasma concentrations in study X2101.

DETAILED DESCRIPTION OF THE INVENTION

The present invention provides drug products in the form of modified-release formulations of AFQ056, which alter the pharmacokinetic profile of AFQ056, resulting in effective and sustained drug concentration over a longer period of time, reducing the peak to trough ratio. The modified release formulations of the present invention have a positive food effect with increased Cmax compared to the fasted state.

A modified release form is a solid oral dosage form that permits the release of the active ingredient over an extended period of time to maintain therapeutically effective plasma levels. The modified release formulation may be a controlled release formulation, one that exhibits substantially zero order release kinetics. It may also be a sustained release formulation, which exhibits first order kinetics.

An immediate release form is a solid oral dosage form that permits the release of most or all of the active ingredient over a short period of time, such as 60 minutes or less, and make rapid absorption of the drug possible.

Dose dumping is an unintended, rapid drug release in a short period of time of the entire amount or of a significant fraction of the active drug substance retained in a release dosage form.

Figure 5A:
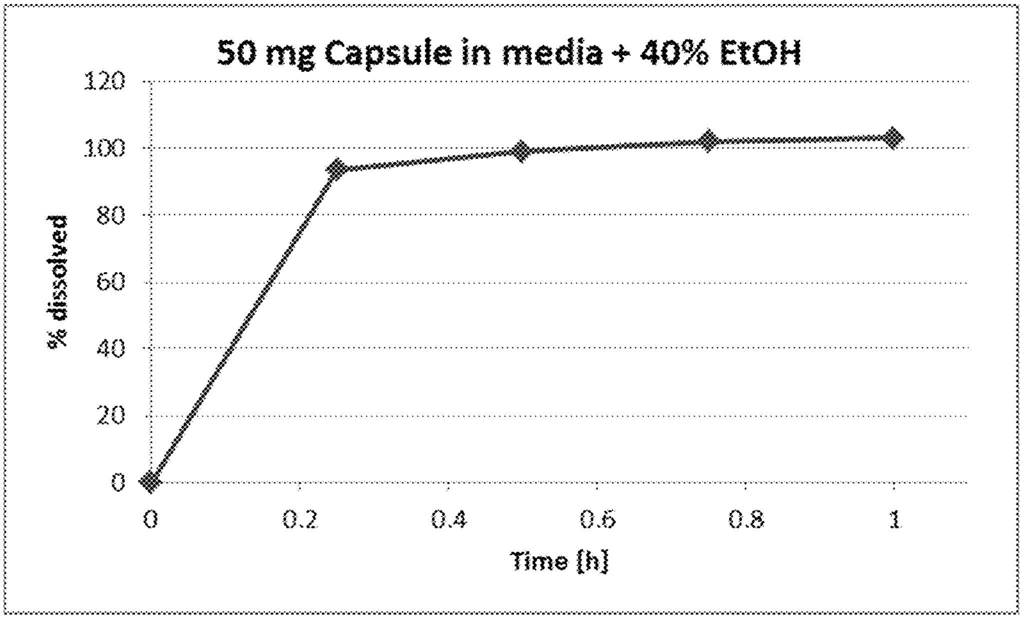
FIG. 5 shows the dissolution profile of the immediate release form (capsule) comprising 50 mg AFQ056. After about 30 minutes in the 0.5% LDAO in water solution containing 40% ethanol, a dissolution of 100% is achieved.
Figure 5B:
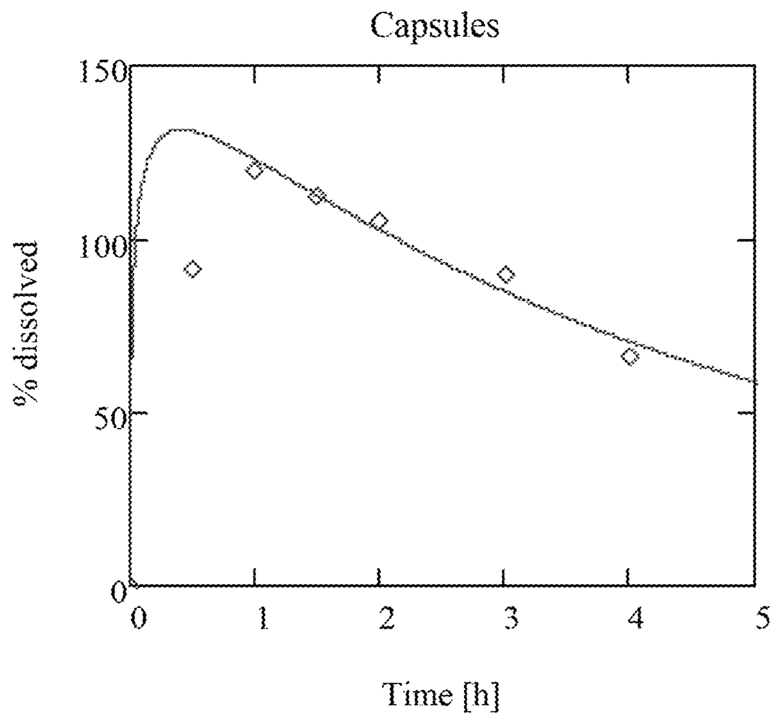
Figure 6A:
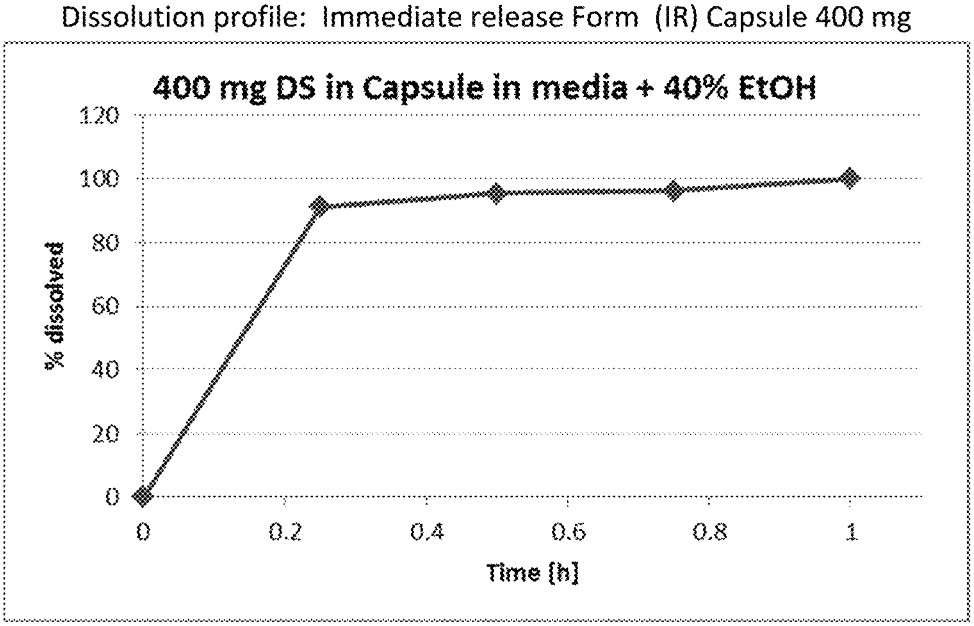
FIG. 6 graphically depicts the dissolution profile of the immediate release form (capsule) comprising 400 mg AFQ. After about 30 minutes in the LDAO in water solution containing 40% ethanol, a dissolution of almost 100% is achieved. In the simulation of human PK parameters (simulation of human PK applying the in-vitro in-vivo correlation model) the Tmax value in the ethanol containing solution is achieved faster and the Cmax and the $AUC_{48h}$ are both higher compared to the observed plasma concentrations in study X2101.
Figure 6B:
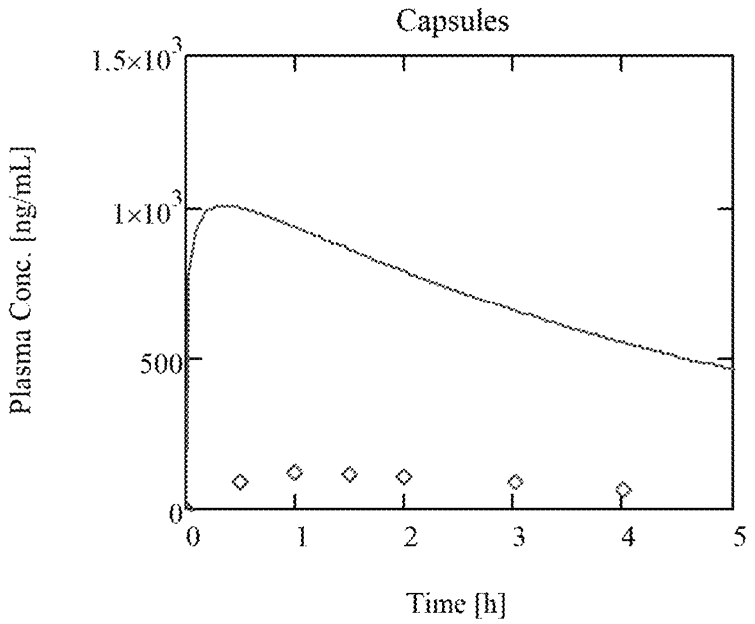

The solubility pattern of AFQ056 was examined (FIG. 1). AFQ056 is hardly soluble in water but soluble in organic solvents such as ethanol. In pure aqueous solutions the solubility of AFQ056 steadily increases with raising ethanol concentrations. The solubility pattern of AFQ056 in a LDAO water-ethanol solution is distinct from the solubility pattern of AFQ056 in a pure aqueous solution only up to an amount of 20% ethanol present in the solution. It was observed that the increase in solubility of AFQ056 by raising the presence of ethanol is even steeper than the solubility of a comparable drug such as aspirin (Roberts et al.; Int. Journal of Pharmaceutics 2007, 332, p. 31-37). Solubilities of AFQ056 are about 0.02 mg/ml in water and raise up to about 53 mg/ml (factor 2500× solubility increase) in ethanol at room temperature. This is in contrast to 8.4 mg/ml for Aspirin in water raising up to about 237 mg/ml in ethanol (factor 28× solubility increase). It was observed that high concentrations of ethanol significantly raise the dissolution rate and thus have an impact on the pharmacokinetic parameters. FIGS. 5 and 6 show that the predicted pharmacokinetic parameters of AFQ056 immediate release forms (50 mg AFQ056 capsule and 400 mg AFQ056 capsule) change dramatically in the presence of ethanol. Tmax is reached faster and both Cmax and $AUC_{48h}$ are higher for an immediate release form in the presence of ethanol. Immediate release forms of AFQ056 have therefore the inherent risk of dose dumping and can create severe consequences for the patient if ethanol-containing beverages are consumed in parallel. Particle size distribution is also an important factor influencing the dissolution of a drug substance and is known to influence the drug release from matrix tablets.

Description of the dynamics of getting AFQ056 into solution is finally related to various factors such as the intrinsic properties of AFQ056, the composition of the described dissolution media, specific properties of HPMC (hypromellose) influencing solubility/dissolution rate of AFQ056 and the resulting viscosity in the surrounding of the solids to be dissolved.

Figure 1A:
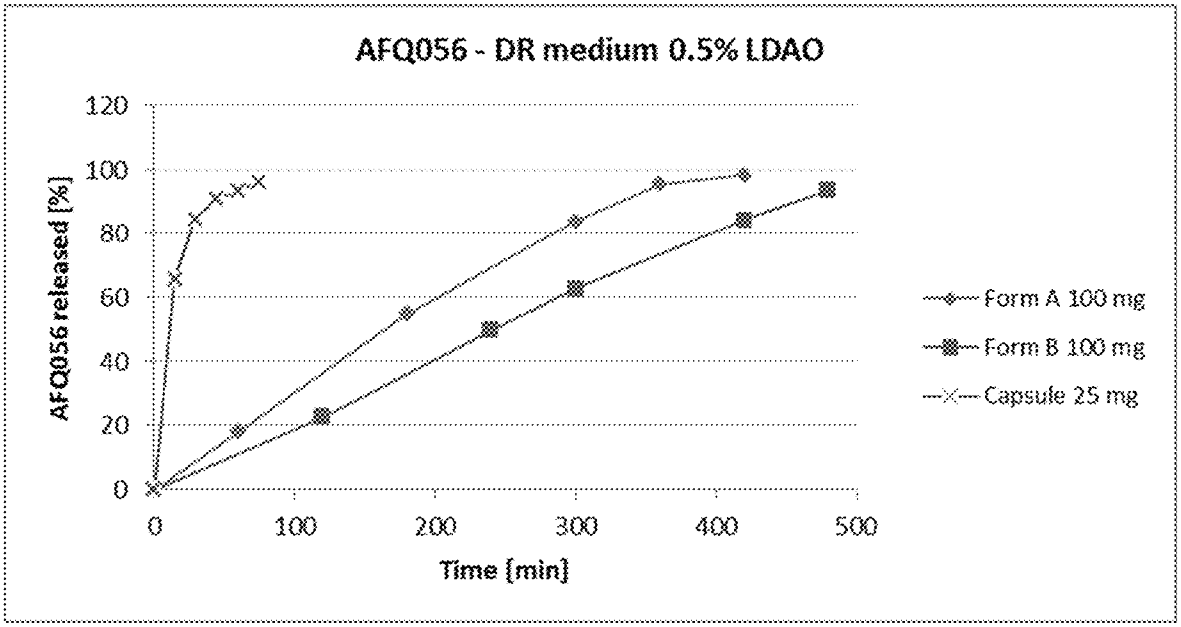
FIG. 1 shows the dissolution profiles and the in vivo-in vitro correlation (IVIVC) of two modified release formulations and of a formulation for a capsule (immediate release form 50 mg). The calculated profiles are in line with the measured human plasma concentrations.
Figure 1B:
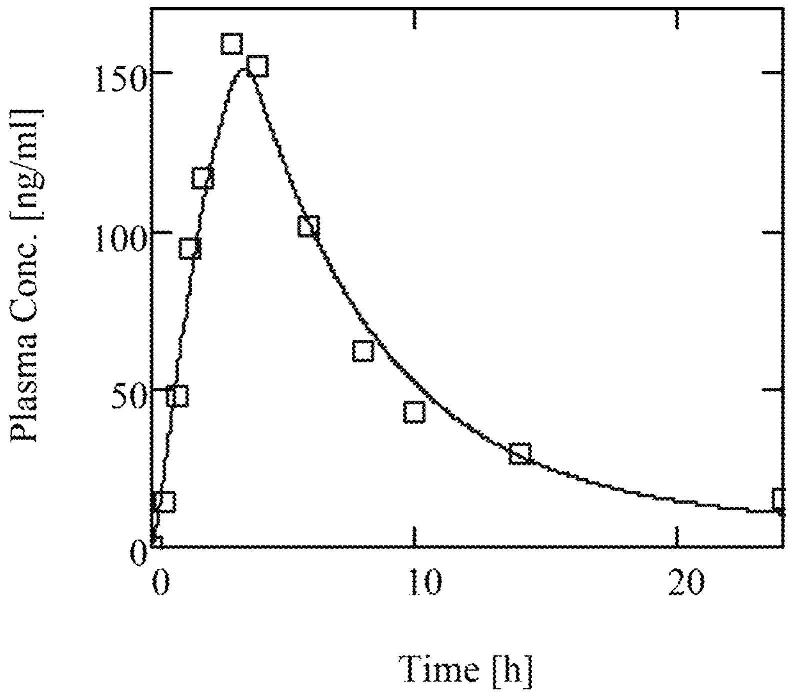
Figure 1C:
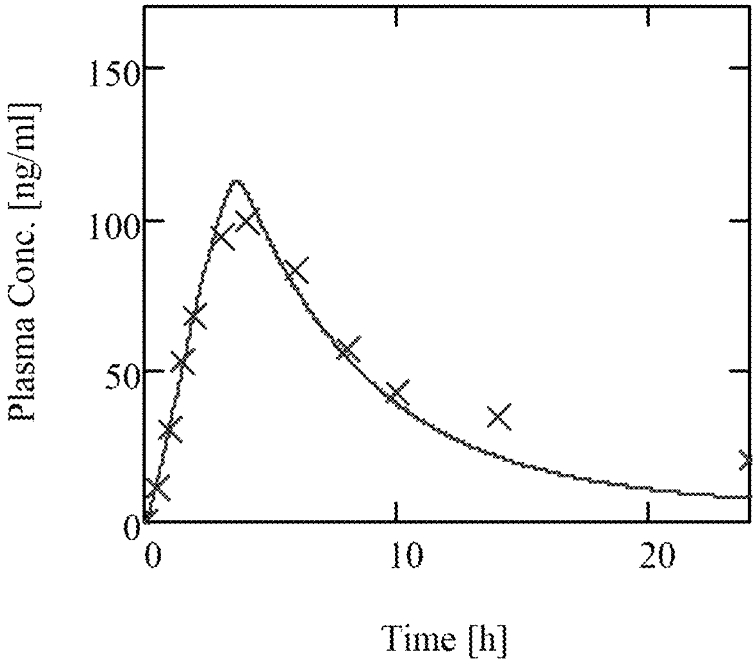
Figure 1D:
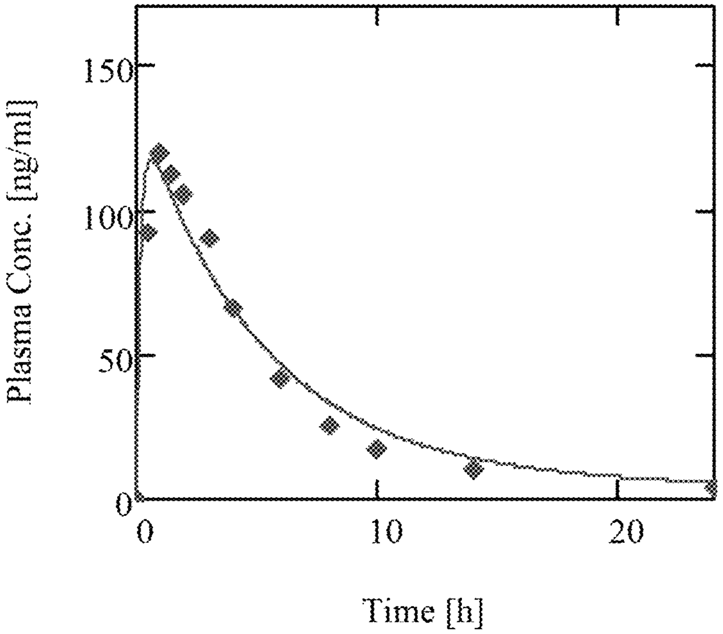
Figure 2:
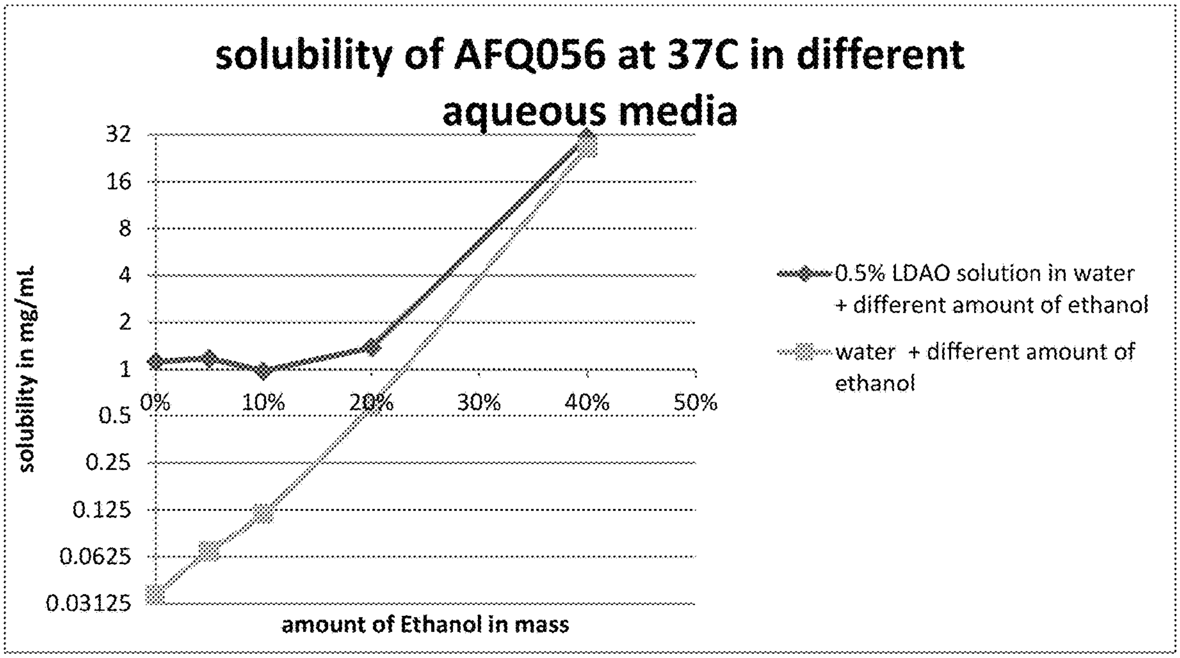
FIG. 2 graphically depicts the solubility of AFQ056 at 37° C. in different aqueous media.
Figure 3:
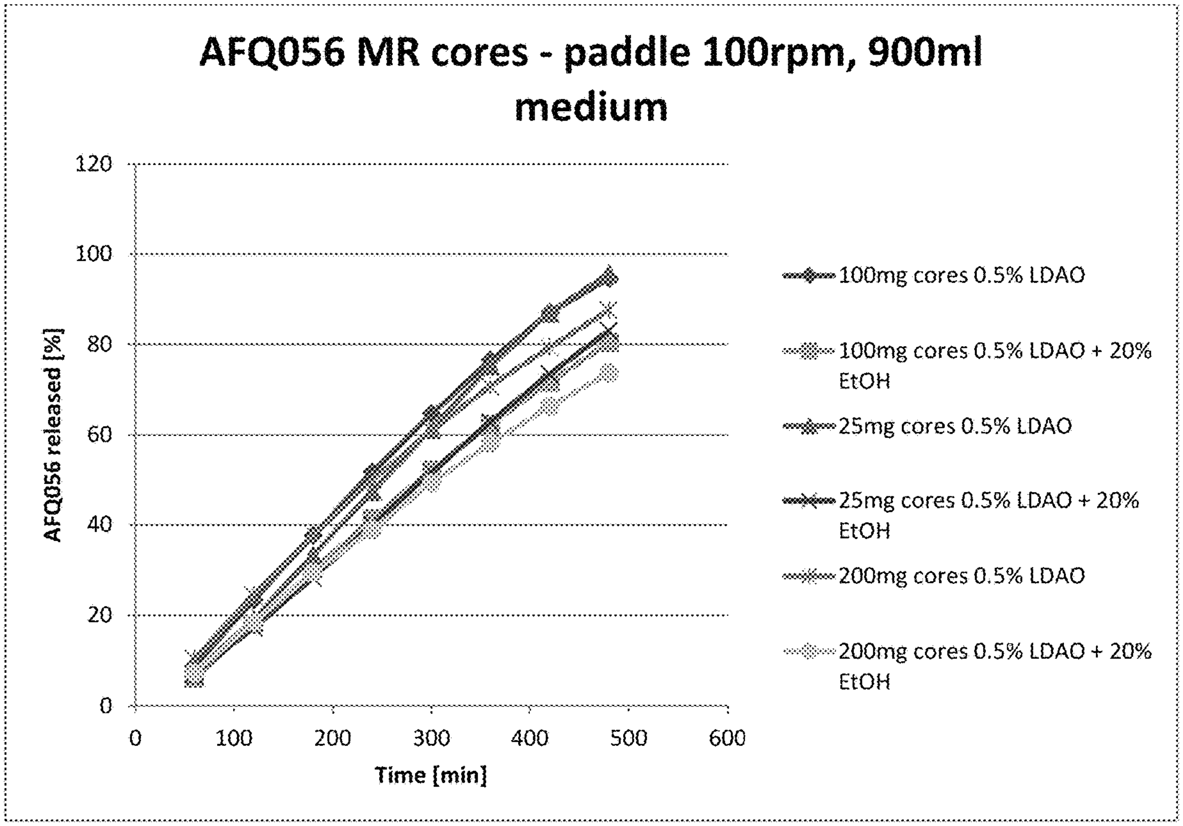
FIG. 3 shows the dissolution rate of the modified release form. All modified release dosage strengths show consistently a lower dissolution rate in the presence of 20% ethanol.
Figure 4:
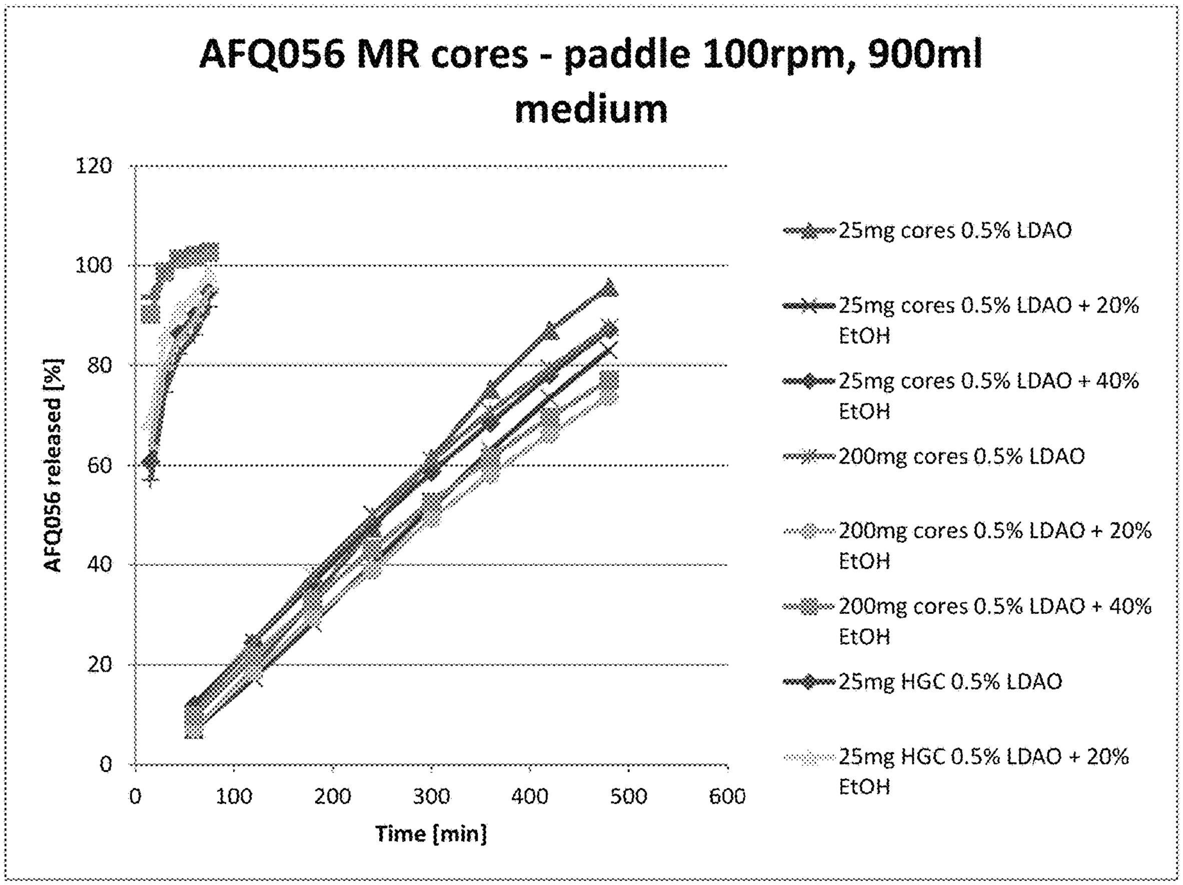
FIG. 4 graphically depicts the dissolution rates of the modified release form and of the immediate release form in the presence of ethanol, the latter consistently showing a trend to faster dissolution rate in the presence of 20% and 40% Ethanol which is expected from solubility at the respective ethanolic concentrations.
Figure 7A:
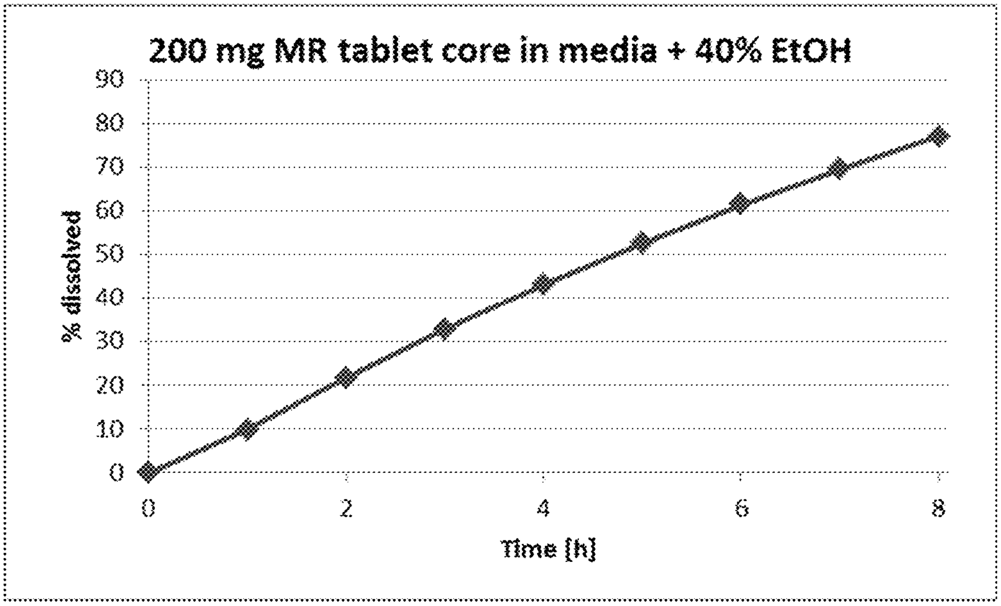
FIG. 7 graphically depicts the dissolution profile of the modified release form comprising 200 mg AFQ056. After 8 hours in the LDAO in water solution containing 40% ethanol, a dissolution of less than 80% was observed. In the simulation of human PK parameters (simulation of human PK applying the in-vitro in-vivo correlation model) the Tmax value in the ethanol containing solution is almost identical and the Cmax and the $AUC_{48h}$ are both almost equal to the observed plasma concentrations in study X2101.
Figure 7B:
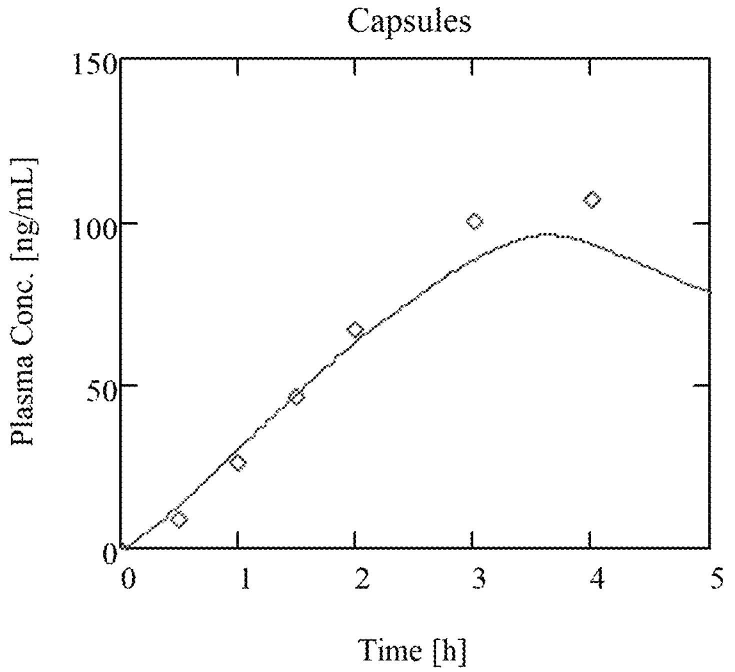

Despite the solubility characteristics of AFQ056 (factor 2500× solubility increase in ethanol compared to water) it was surprisingly found that the release rate of the modified release formulations of the present invention is similar or even slower in ethanol than that in water. FIG. 3 and FIG. 4 illustrate the release pattern of the present formulations in ethanol containing solutions. It is speculated that the combination of several factors such as the presence of hypromellose, the particle size and the size distribution of the drug substance result in the observed release pattern of the AFQ056 modified release formulations. Surprisingly the predicted pharmacokinetic parameters of the modified release formulation remain almost equal in the presence of ethanol (FIG. 7). It is therefore shown that the modified release form is dose dumping resistant in the presence of ethanol.

AFQ056 may be prepared as described in WO 03/047581, the contents of which are incorporated by reference. In the modified release formulations of the present invention, AFQ056 is present as free base.

Excipients that may be used in the formulations of the present invention are standard excipients commonly used for tablet dosage forms and include but are not limited to fillers, modified release agents, disintegrants, lubricants, glidants, solvents, viscosity agents, emulsifiers, binding agents, buffers, bulking agents, coloring agents, taste-improving agents, flow agents, fillers, absorbents and water soluble coatings.

Examples of fillers which may be used in the formulations of the present invention include but are not limited to lactose monohydrate, dibasic calcium phosphate, calcium carbonate, sugar alcohols (e.g. mannitol), microcrystalline cellulose and starch. Preferably, lactose monohydrate is used as a filler.

Examples of modified release agents which may be used in the formulations of the present invention without being resistant to dose dumping in the presence of ethanol include but are not limited to hydroxy propyl methylcellulose (HPMC), also known as hypromellose, (a) hydrophilic carbohydrate macromolecules (acacia, agar, alginic acid, carboxymethylcellulose, carrageenans, dextrin, gellan gum, guar gum, hydroxyethyl cellulose, hydroxypropyl cellulose, hypromellose, maltodextrin, methylcellulose, pectin, propylene glycol alginate, sodium alginate, starch, tragacanth, and xanthan gum) and (b) noncarbohydrate hydrophilic macromolecules, including gelatin, povidone carbomers, polyethylene oxide, and polyvinyl alcohol. Modified release agents which may be used in formulations of the present invention that are dose dumping resistant in the presence of ethanol are preferably, hypromellose such as hypromellose type 2208 and type 2910 is used. More preferably, Methocel K100 Premium LV CR, Methocel K4M Premium CR, Methocel K15M Premium CR, Methocel K100M Premium CR, Methocel E4M Premium CR, and Methocel E10M Premium CR is used, in sum characterized by viscosities between about 80 to about 120000 cP (20° C.).

Examples of binders which may be used in the formulations of the present invention include but are not limited to cellulose derivatives (e.g. hypromellose, hydroxypropylcellulose, methylcellulose), gelatin, polyvinylpyrrolidone, copovidone, starch, sucrose and polyethylene glycol. In a preferred embodiment hypromellose, type 2910, is used.

Various glidants may be used in the formulations of the present invention and include e.g. silicon dioxide as precipitated silica and as colloidal silica, colloidal silicon dioxide. Preferably colloidal silicon dioxide e.g., Aerosil® is used.

Various disintegrants may be used in the formulations of the present invention, including, but not limited to, sodium starch glycolate, carboxymethylcellulose sodium/croscarmellose Sodium, crospovidone/cross-linked polyvinylpyrrolidone, starches, celluloses and pullulan. Preferably, sodium starch glycolate is used.

Examples of lubricants which may be used in the formulations of the present invention, include but are not limited to magnesium stearate, calcium stearate, zinc stearate, stearic acid, sodium benzoate, sodium stearyl fumarate, sodium lauryl sulfate, hydrogenated vegetable oil, glycerides (glyceryl behenate and distearate). In a preferred embodiment, magnesium stearate is used as lubricant.

Coatings which may be used in the formulations of the present invention include but are not limited to hypromellose, hydroxypropyl cellulose, methylcellulose, povidone, polyvinyl alcohol, Macrogol poly(vinyl alcohol) grafted copolymer and starches. In a preferred embodiment hypromellose, macrogol 4000/polyethylene glycol 4000, talc, iron oxide (red, yellow, black), and titanium dioxide is used.

The modified release formulations of the present invention may be made by mixing, aqueous granulation, screening, drying, tablet compression and film-coating steps, all of which are well known in the art.

For example, the modified release formulations are made by mixing AFQ056, filler, binder and disintegrant in a high shear granulator for approximately 5 minutes. Purified water is added under mixing and the mixture kneaded in a high shear granulator. The granulate is then passed through a screen using a screening mill and dried in a fluid bed dryer.

After drying, the granulate is mixed with filler, modified release agent and glidant, followed by consecutive sieving using a screening mill and mixing in a diffusion mixer (tumble). A lubricant is sieved and then added to the mixture from the diffusion mixer. The composition is then formed by final mixing.

The resulting granules of the composition may have a diameter from a few microns to a few hundred microns; e.g., diameters of at most about 450 microns, e.g., to 450 microns, preferably 50-200 μm, most preferably, 100-200 μm.

A narrow particle size distribution is preferred. For example, a preferred particle size distribution is $\times 10 \leq 50$ μm, $\times 50 \leq 100$-150 μm and $\times 90 \leq 200$-450 μm, i.e., 10% of particles are smaller than 50 μm, 50% of particles are smaller than 150 μm, and 90% of particles are smaller than 450 μm.

The blend is then compressed into tablet cores using a rotary tablet press. A coating mixture in purified water is dispersed and the tablet cores are film coated in a pan coater with perforated coating system.

Preferably, the modified release formulations are made by mixing AFQ056, lactose monohydrate, hypromellose (type 2208) and sodium starch glycolate in a high shear granulator for approximately 5 minutes. Purified water is added under mixing and the mixture kneaded in a high shear granulator. The granulate is then passed through a screen using a screening mill and dried in a fluid bed dyer.

After drying, the granulate is mixed with hypromellose (type 2208), lactose monohydrate and colloidal silicon dioxide followed by consecutive sieving using a screening mill and mixing in a diffusion mixer (tumble). The magnesium stearate is sieved and then added to the mixture from the diffusion mixer. The composition is formed by final mixing. The blend is then compressed into tablet cores using a rotary tablet press. A coating mixture in purified water is dispersed and the tablet cores are film coated in a pan coater with perforated coating system.

The modified release formulations of the present invention are useful in treating Parkinson's disease (PD) and effective amounts of such formulations are administered to such patients.

The phrases "effective amount", "amount effective" or "amounts effective" describe concentrations or amounts of the drug substance according to the present invention, which may be used to produce a favorable change in L-dopa induced motor complications such as dyskinesias (LIDs). The total daily effective amount(s) can be administered in divided doses (e.g., multiple capsules or tablets).

Preferably, the total daily effective amount is delivered in a single dosage form (e.g., one tablet), which in total, delivers an effective amount of AFQ056. Thus, the drug products of the present invention may be administered multiple times a day, twice a day (b.i.d.) or once a day (o.d.). A once a day dose is preferable since it may lead to increased patient compliance.

In accordance with the present invention, a single dosage form of the modified release formulation of the present invention provides AFQ056 in an amount of about 25 mg to about 250 mg. Preferably, a single dosage form of the modified release formulation of the present invention provides AFQ056 in an amount of about 50 to about 200 mg.

The drug products of the present invention may be used to treat nervous system disorders mediated in full or in part by mGluR5. Such disorders include Parkinson's disease L-dopa induced dyskinesia, Fragile X syndrome (Martin-Bell syndrome), dyskinesia in Fragile X syndrome, obsessive compulsory disorders, autism, cystitis, acute, traumatic and chronic degenerative diseases of the nervous system such as Parkinson's disease, senile dementia, Alzheimer's disease, Huntington's chorea, amyotrophic lateral sclerosis and multiple sclerosis, psychiatric diseases such as schizophrenia and anxiety, depression, pain, itch and drug abuse, e.g. alcohol and nicotine abuse and cocaine use disorders.

The drug products of the present invention may be used in the manufacture of a medicament for the treatment of Parkinson's disease L-dopa induced dyskinesia, Fragile X syndrome (Martin-Bell syndrome), dyskinesia in Fragile X syndrome, obsessive compulsory disorders, autism, cystitis, and for the treatment, prevention or delay of progression of acute, traumatic and chronic degenerative processes of the nervous system, such as Parkinson's disease, senile dementia, Alzheimer's disease, Huntington's chorea, amyotrophic lateral sclerosis and multiple sclerosis, psychiatric diseases such as schizophrenia and anxiety, depression, pain, itch and drug abuse such as alcohol and nicotine abuse and cocaine use disorders.

In a preferred embodiment, the drug products of the present invention are used to treat Parkinson's Disease-Levodopa Induced Dyskinesia (PD-LID).

The following examples further illustrate the invention, which are not meant in any way to limit the scope thereof.

Example 1

The following formulations (tablet core compositions) of AFQ056 are made:

TABLE 1

| | IR-Caps [mg/dose] | Form A [mg/dose] | Form B [mg/dose] | Form C [mg/dose] |
|---|---|---|---|---|
| AFQ056 | 100.00 | 100.00 | 100.00 | 99.00 |
| Lactose monohydrate | 100.00 | 22.00 | 22.00 | 21.78 |
| Microcrystalline Cellulose | 20.00 | — | — | — |
| Sodium Starch glycolate | 16.25 | 12.50 | 12.50 | 12.375 |
| Hypromellose | 10.00 | 42.80 | 69.50 | 71.775 |
| Colloidal Silicon Dioxide | 1.25 | 0.90 | 1.00 | 0.99 |
| Magnesium stearate | 2.50 | 1.80 | 2.00 | 1.98 |
| Total | 250.00 | 180.00 | 207.00 | 207.90 |
| | IR-Caps [%] | Form A [%] | Form B [%] | Form C [%] |
| AFQ056 | 40.00 | 55.56 | 48.31 | 47.62 |
| Hypromellose | 4.00 | 23.78 | 33.57 | 34.52 |
| Lactose monohydrate | 40.00 | 12.22 | 10.63 | 10.48 |
| Microcrystalline Cellulose | 8.40 | — | — | — |
| Sodium Starch glycolate | 6.50 | 6.94 | 6.04 | 5.95 |
| Magnesium stearate | 1.00 | 1.00 | 0.97 | 0.95 |
| Colloidal Silicon Dioxide | 0.50 | 0.50 | 0.48 | 0.48 |

Since previous oral formulations have exhibited an increased exposure upon concomitant intake of a high-fat meal, the extent of which has been found to be formulation-dependent, this study is designed to assess the food-effect (by administration of a high fat breakfast) on the PK of the modified release forms.

The effect of a high-fat breakfast on the pharmacokinetics and relative bioavailability of three prolonged release formulations of AFQ056 at a single dose of –100 mg (with reference to the fasted state PK) is assessed. In addition, the tolerability of three different prolonged release formulations of AFQ056 at a single dose of 100 mg under fasted and fed conditions is tested An open-label, randomized, five periods, seven treatments cross-over study in healthy subjects is conducted. A total of forty five (45) subjects are enrolled to obtain data on at least 30 completers. Each subject receives a total of 5 single doses of AFQ056; three doses under fasted conditions and two doses under fed conditions.

The study consists of a screening period (up to 27 days), 5 baseline periods, 4 wash out periods of 7-2 days inclusive. 5 treatment periods followed by a Study Completion Evaluation 5-10 days (inclusive) after the last drug administration.

Subjects who meet the eligibility criteria at screening are admitted to baseline evaluations for treatment period 1. Subjects are admitted to the study site at least 12 hours prior to dosing in each period for baseline evaluations. All baseline safety evaluation results must be available prior to dosing. After an overnight fast, subjects are randomized to one of the treatment sequence (Table 2).

Treatment 1: AFQ056 100 mg Form-A. fasted

Treatment 2: AFQ056 100 mg Form-A, fed

Treatment 3: AFQ056 100 mg Form-B. fasted

Treatment 4: AFQ056 100 mg Form-B. fed

Treatment 5: AFQ056 99 mg Form-C. fasted

Treatment 6: AFQ056 99 mg Form-C, fed

Treatment 7: AFQ056 50 mg Capsule, fasted

TABLE 2

| | Treatment sequenc per | | | | |
|---|---|---|---|---|---|
| Sequence | Period 1 | Period 2 | Period 3 | Period 4 | Period 5 |
| 1 | 1 | 2 | 3 | 4 | 7 |
| 2 | 2 | 3 | 4 | 7 | 1 |
| 3 | 3 | 4 | 7 | 1 | 2 |
| 4 | 4 | 7 | 1 | 2 | 3 |
| 5 | 7 | 1 | 2 | 3 | 4 |
| 6 | 1 | 2 | 5 | 6 | 7 |
| 7 | 2 | 5 | 6 | 7 | 1 |
| 8 | 5 | 6 | 7 | 1 | 2 |
| 9 | 6 | 7 | 1 | 2 | 5 |
| 10 | 7 | 1 | 2 | 5 | 6 |
| 11 | 3 | 4 | 5 | 6 | 7 |
| 12 | 4 | 5 | 6 | 7 | 3 |
| 13 | 5 | 6 | 7 | 3 | 4 |

TABLE 2-continued

| Treatment sequenc per | | | | | |
|---|---|---|---|---|---|
| Sequence | Period 1 | Period 2 | Period 3 | Period 4 | Period 5 |
| 14 | 6 | 7 | 3 | 4 | 5 |
| 15 | 7 | 3 | 4 | 5 | 6 |

Following each single dose of AFQ056, pharmacokinetic assessments are made up to 72 h post dose. A wash-out period of 7±2 days inclusive separates each treatment period. The washout period is calculated between dose to dose and baseline of subsequent period can overlap with the $5^{th}$ day after dosing.

The total study duration for each subject lasts a minimum of 53 days and a maximum of 70 days from screening to study completion. Subject are domiciled for approximately 20 days in total (4 days for each period) for all sequences.

The study has a 3-Latin, 5-sequences×5-period open-label design that is suitable for comparing the pharmacokinetics including relative bioavailability of three modified release formulations of AFQ056. The immediate release capsule formulation (size O, IR) is used as a reference to enable comparisons with data obtained in previously completed trials. This study design allows the comparison of pharmacokinetic profile of AFQ056 from three modified release (MR) formulations relative to the IR formulation under fasted conditions, and to assess the food effect on the pharmacokinetics of the three MR forms. Latin-square design is selected as it offers maximum precision of comparison across different treatments with minimum number of study subjects. The cross-over design permits investigation of all five treatment conditions within each subject and is used to account for interindividual variability. A wash out period of at least 5 days ensures complete washout of AFQ056 based on a half life of 7 to 17 hours for 50 mg and for 100 mg doses. Sampling for 72 hours post dose is considered sufficient for characterizing the PK profiles of all formulations, including the MR forms.

Figure 9:
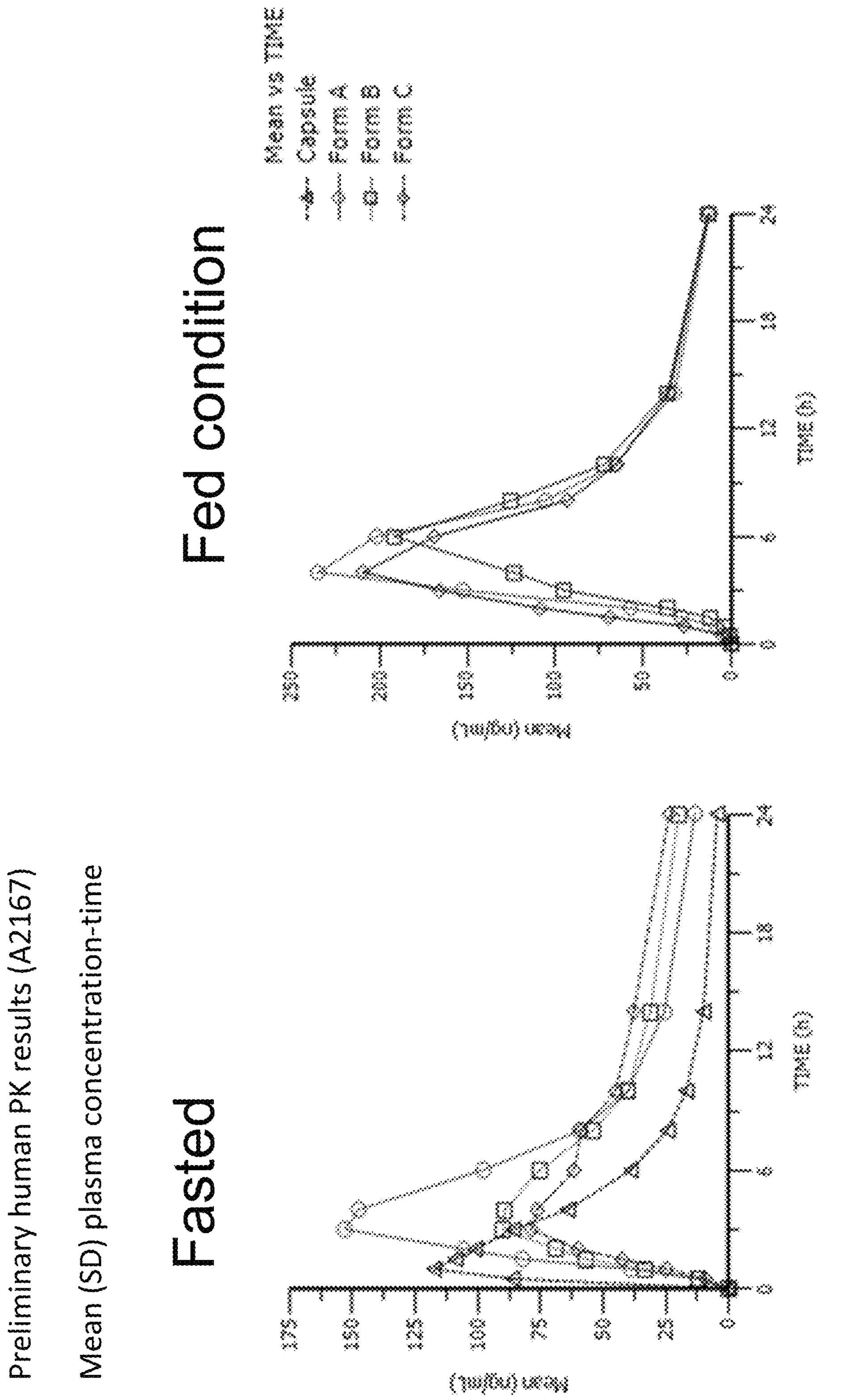
FIG. 9 graphically depicts mean (SD) plasma concentration-time profiles of modified release forms compared with a capsule immediate release form, under fasted and fed conditions.

Comparisons of the concentration-time profile for the fasted and fed conditions for all formulations are provided in FIG. 9.

Figure 10:
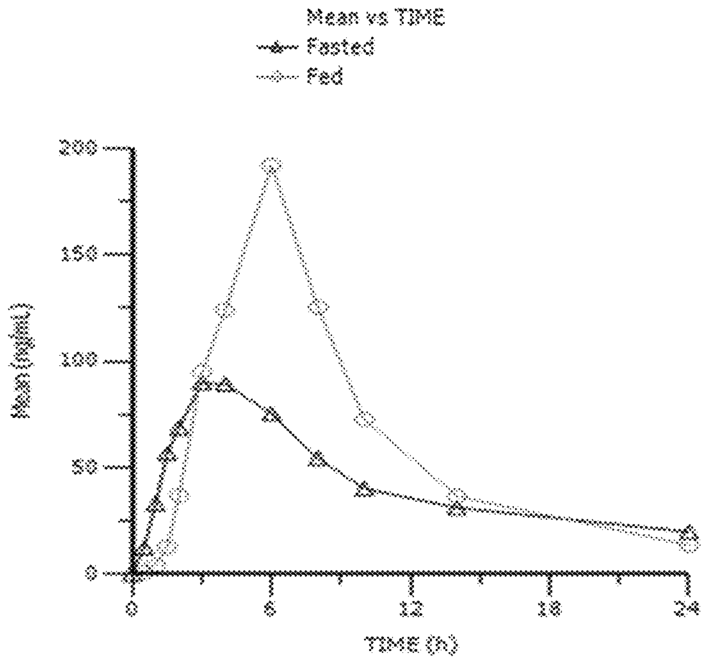
FIG. 10 graphically depicts mean (SD) plasma concentration-time profile of a selected modified release formulation B under fasted versus fed conditions.

Mean (SD) plasma concentration-time profile of selected modified release formulation form B, fasted versus fed, is depicted in FIG. 10.

The results of the non-compartmental PK analysis are summarized in Table 3. For better comparability the PK parameters were normalized to dose where necessary.

TABLE 3

Key PK parameters (average +/− SD) from preliminary analysis for market formulation (MF) IR and modified-release (MR) formulation

| | Food State | n | Tmax [1] [h] | Cmax/Dose [ng/mL] | AUC0-24 h/dose [ng*h/mL] | Ratio Cmax/AUC |
|---|---|---|---|---|---|---|
| MR Formulation A | Fasted | 23 | 3.0 (2.0-6.0) | 1.760 (0.754) | 13.027 (4.950) | 0.137 (0.33) |
| | Fed | 23 | 4.0 (1.5-10.0) | 3.437 (1.777) | 17.612 (9.919) | 0.206 (0.054) |
| MR Formulation B | Fasted | 21 | 4.0 (1.5-6.0) | 1.076 (0.456) | 12.165 (5.766) | 0.092 (0.023) |
| | Fed | 21 | 6.0 (2.0-24.0) | 2.555 (1.067) | 16.070 (7.418) | 0.168 (0.051) |
| MR Formulation C | Fasted | 21 | 3.0/ 2.0-8.0) | 0.926 (0.281) | 12.828 (6.989) | 0.083 (0.036) |
| | Fed | 22 | 4.0 (2.0-8.0) | 2.570 (0.868) | 17.595 (7.600) | 0.158 (0.047) |
| IR Capsule | Fasted | 33 | 1.0 (0.5-6.0) | 2.955 (1.340) | 14.071 (6.956) | 0.221 (0.070) |

[1] values for Tmax are median (range)

Results indicate that modified release (MR) forms show a decrease in Cmax (at Tmax) with very little loss of AUC. Cmax/AUC ratios are favorable for all modified release forms over the intermediate release (IR) form with the best ratio for Form B and C. All MR forms have a positive food effect with increased Cmax compared to the fasted state.

Example 2

The tablet core is formulated using common excipients for such pharmaceutical dosage forms. Release of the drug substance from the tablet core occurs through an erosion and diffusion mechanism, and is controlled by the hypromellose (type 2208) content of the formulated product. A pharmacokinetic study is performed using different 100 mg modified release tablet formulations in order to evaluate the impact of delaying release of the active ingredient.

The same ratio of excipients in the 100 mg tablet core is used to create the additional dosage strengths. The lower dosage strengths e.g. 25 mg, 50 mg and 75 mg use lactose monohydrate as compensation for drug substance in order to maintain the tablet weight and size. The tablet cores of dosage strengths less than or equal to 100 mg are compressed to round tablets possessing a diameter of 8 mm.

For the higher dosage strengths e.g. 150 mg, 200 mg and 250 mg, the tablet weight and size are increased. The same formulation principle is applied i.e. using lactose monohydrate as compensation for drug substance. The tablet cores of dosage strengths more than 100 mg are compressed to round tablets possessing a diameter of 11 mm. Table 4 summarizes the tablet core composition of the different dosage strengths.

TABLE 4

Tablet core composition overview for AFQ056 MR FCT

| | Amount per film-coated tablet (mg) | | | | | |
|---|---|---|---|---|---|---|
| Ingredient | 25 mg | 50 mg | 100 mg | 150 mg | 200 mg | 250 mg |
| AFQ056 | 25.00 | 50.00 | 100.00 | 150.00 | 200.00 | 250.00 |
| Lactose monohydrate | 96.30 | 71.20 | 22.00 | 152.00 | 100.50 | 55.00 |
| Sodium starch glycolate | 3.13 | 6.25 | 12.50 | 18.75 | 25.00 | 31.25 |
| Hypromellose | 79.48 | 76.35 | 69.5 | 120.75 | 115.90 | 105.25 |
| Magnesium Stearate | 2.00 | 2.00 | 2.00 | 4.50 | 4.40 | 4.50 |
| Colloidal silicon dioxide | 1.00 | 1.00 | 1.00 | 2.00 | 2.20 | 2.00 |
| Core tablet weight | 206.9 | 206.8 | 207.0 | 448.0 | 448.0 | 448.0 |

Figure 8A:
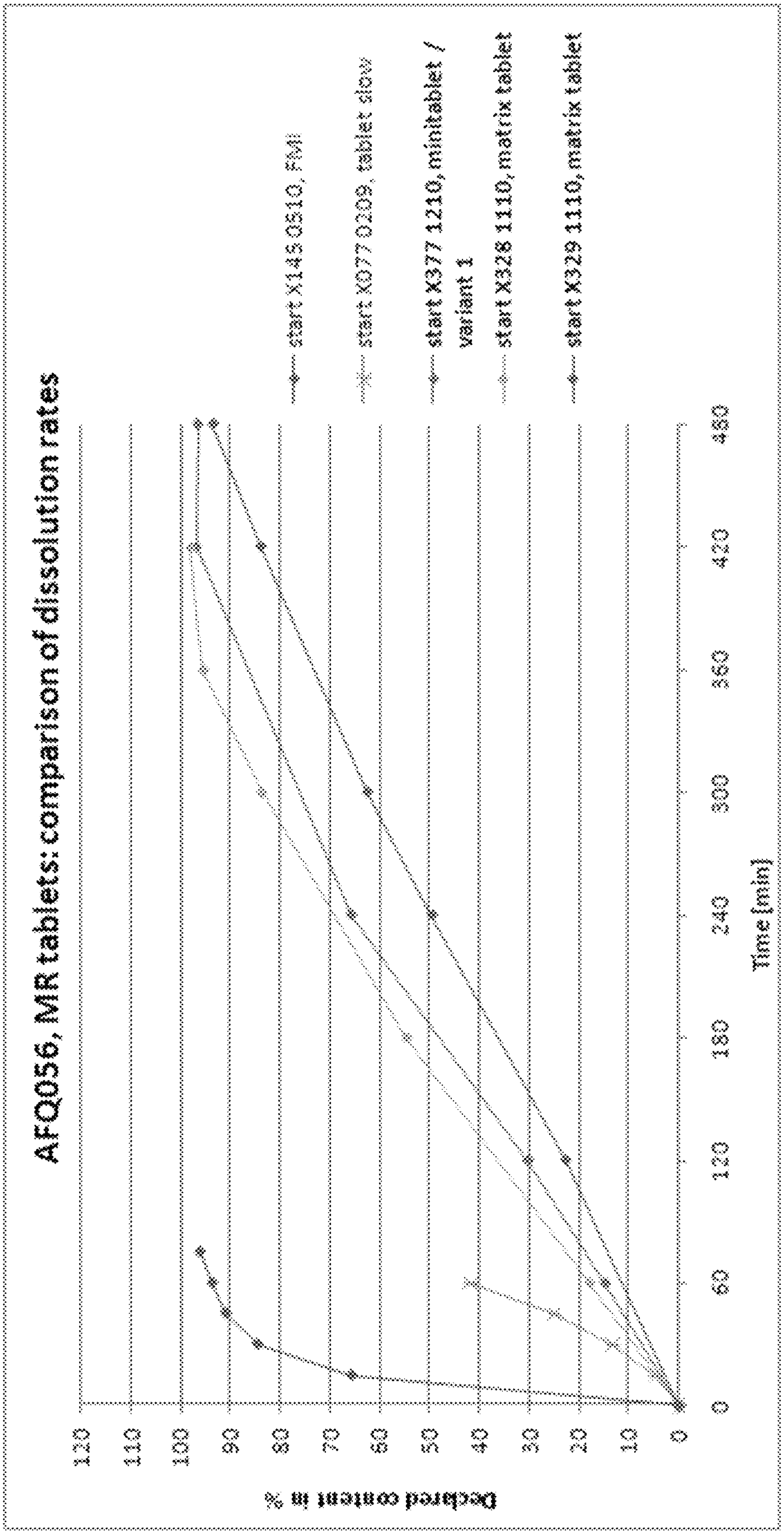
FIG. 8 provides a comparative dissolution profile of AFQ056 modified release film-coated tablets studied in a human experiment. It is shown that the modified release tablets release the active pharmaceutical ingredient in a controlled fashion almost linearly during several hours. At the end of a period of 6 hours, or at the end of a period of 7 hours, at least 80% of the active pharmaceutical ingredient has been released.

Dissolution of AFQ056 modified release film-coated tablets occurs through an erosion and diffusion mechanism, with a target release time of approximately 6 to 7 hours for >80% of the active ingredient (Table 5). The dissolution method uses dissolution apparatus 2 (paddle) at 100 rpm with 900 ml of Water+0.5% LDAO. Comparative dissolution profiles for AFQ056 modified release film-coated tablets are provided in FIG. 8.

TABLE 5

Dissolution results for AFQ056 MR Film-coated tablets

| | Amount of AFQ056 released (%) in: | | | | |
|---|---|---|---|---|---|
| Strength/Batch No. | 60 min | 180 min | 240 min | 360 min | 420 min |
| 25 mg/X217 0911 | 13.9 | 51.4 | 67.3 | 90.1 | 95.6 |
| 50 mg/X218 0911 | 19.1 | 59.4 | 75.9 | 94.6 | 98.6 |
| 100 mg/X220 0911 | 16.1 | 58.2 | 73.8 | 95.3 | 98.6 |
| 150 mg/X221 0911 | 20.4 | 61.1 | 76.5 | 95.2 | 98.1 |
| 200 mg/X266 1111 | 20.0 | 57.4 | 71.5 | 90.8 | 95.4 |

Example 3

Particle size distribution is an important factor in dissolution of the modified release forms of the present invention. The following experiments are performed to in order to determine how particle size effects dissolution at various time points.

Figure 11:
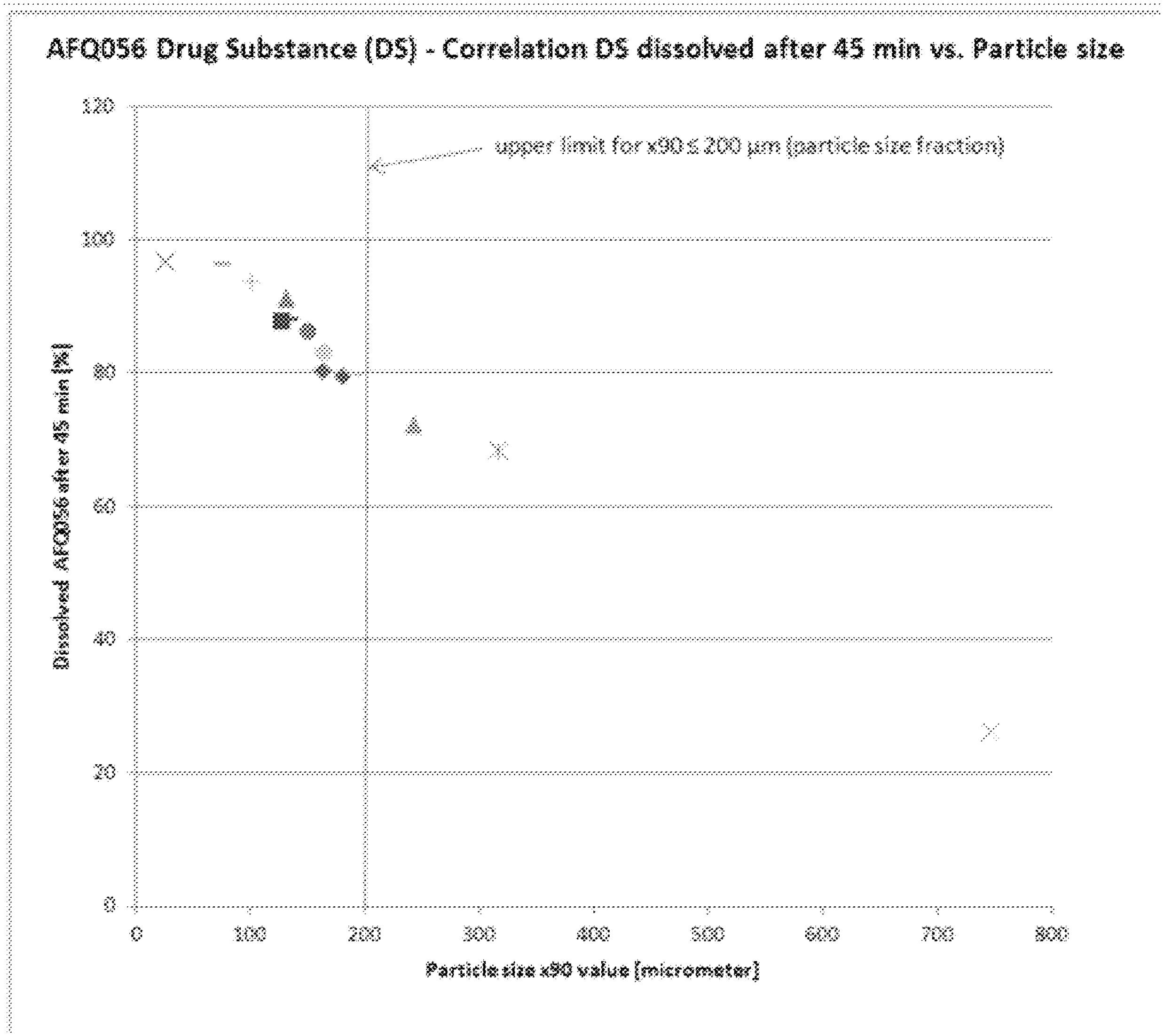
FIG. 11 graphically depicts percent AFQ056 drug substance dissolved after 45 minutes versus AFQ056 drug substance particle size ×90 value (90% of the particles are smaller or equal).

FIG. 11 graphically depicts the percentage of AFQ056 dissolved after 45 minutes versus particle size at ×90. As can be discerned from the figure, particle size distribution is a key factor in dissolution rate and thus the performance of the MR Form. The drug substance has a particle size distribution of ×10≤50 μm, ×50≤100 μm and ×90≤200 μm.

The invention claimed is:

1. A stable, modified release single dosage form comprising:

(a) from about 50 mg to about 200 mg of (−)-(3aR,4S,7aR)-4-hydroxy-4-m-tolylethynyl-octahydro-indole-1-carboxylic acid methyl ester in free base form as an active pharmaceutical ingredient, wherein the active pharmaceutical ingredient has a D10 particle size of less than or equal to 50 μm and a D50 particle size of less than or equal to 100 μm, and a D90 particle size of less than or equal to 200 μm;

(b) from about 69 mg to about 135 mg of a modified release agent, the modified release agent being hydroxypropyl methylcellulose;

(c) from about 20 mg to about 160 mg of lactose monohydrate;

(d) from about 3 mg to about 38 mg of sodium starch glycolate;

(e) from about 2 mg to about 4.5 mg of magnesium stearate;

(f) from about 1 mg to about 2.2 mg of colloidal silicone dioxide; and (g) a dissolution profile of the active pharmaceutical ingredient when tested using United States Pharmacopeia (USP) Apparatus 2 (paddle) at 37° C. in 900 mL of an aqueous solution containing 0.5% lauryldimethylamine N-oxide (LDAO) and water at 100 revolutions per minute (rpm) characterized by release of:

(i) from 14% to 20% of the active pharmaceutical ingredient at 60 minutes;

(ii) from 51% to 61% at 180 minutes;

(iii) from 67% to 77% at 240 minutes;

(iv) from 90% to 95% at 360 minutes; and (v) from 95% to 99% at 420 minutes; and further characterized by releasing less than 80% of the active pharmaceutical ingredient at 420 minutes when tested under identical conditions except that the aqueous solution contains 0.5% LDAO, water, and from 20% to 40% ethanol.

2. The stable, modified release single dosage form of claim 1, having a total weight of from about 180 mg to about 448 mg, wherein the stable, modified release single dosage form is a compressed tablet.

3. The stable, modified release single dosage form of claim 2, wherein the compressed tablet has a diameter of about 8 mm.

4. The stable, modified release single dosage form of claim 1, further comprising a coating.

5. The stable, modified release single dosage form of claim 4, wherein the coating comprises hydroxypropyl methylcellulose, hydroxypropyl cellulose, methylcellulose, povidone, polyvinyl alcohol, macrogol poly(vinyl alcohol) grafted copolymer, starches, or combinations thereof.

* * * * *